US009623092B2

(12) United States Patent
Schriemer (10) Patent No.: US 9,623,092 B2
(45) Date of Patent: Apr. 18, 2017

(54) TREATMENT OF GLUTEN INTOLERANCE AND RELATED CONDITIONS

(71) Applicant: David Schriemer, Chestermere (CA)

(72) Inventor: David Schriemer, Chestermere (CA)

(73) Assignee: NEPETX, LLC, Destin, FL (US)

(*) Notice: Subject to any disclaimer, the term of this patent is extended or adjusted under 35 U.S.C. 154(b) by 0 days.

(21) Appl. No.: 13/912,077

(22) Filed: Jun. 6, 2013

(65) Prior Publication Data

US 2014/0140980 A1   May 22, 2014

Related U.S. Application Data

(60) Provisional application No. 61/729,210, filed on Nov. 21, 2012, provisional application No. 61/797,040, filed on Nov. 27, 2012.

(51) Int. Cl.
*A61K 38/48* (2006.01)
*A23L 33/10* (2016.01)
*A23L 33/105* (2016.01)
*A23L 29/00* (2016.01)

(52) U.S. Cl.
CPC ............ *A61K 38/488* (2013.01); *A23L 29/06* (2016.08); *A23L 33/10* (2016.08); *A23L 33/105* (2016.08); *C12Y 304/23012* (2013.01); *A23V 2002/00* (2013.01)

(58) Field of Classification Search
None
See application file for complete search history.

(56) References Cited

U.S. PATENT DOCUMENTS

| | | | |
|---|---|---|---|
| 5,618,564 A * | 4/1997 | Kimura et al. | 424/653 |
| 7,320,788 B2 * | 1/2008 | Shan et al. | 424/94.6 |
| 7,628,985 B2 | 12/2009 | Shan et al. | |
| 7,910,541 B2 | 3/2011 | Hausch et al. | |
| 7,943,312 B2 | 5/2011 | Hausch et al. | |
| 8,119,125 B2 | 2/2012 | Gass | |
| 8,143,210 B2 | 3/2012 | Shan et al. | |
| 8,148,105 B2 | 4/2012 | Vora et al. | |
| 9,005,610 B2 | 4/2015 | Schriemer et al. | |
| 2010/0011456 A1 * | 1/2010 | Mathur et al. | 800/15 |
| 2010/0322912 A1 * | 12/2010 | Khosla et al. | 424/94.2 |
| 2012/0225050 A1 * | 9/2012 | Knight et al. | 424/94.64 |
| 2015/0265686 A1 | 9/2015 | Schriemer | |
| 2015/0290301 A1 | 10/2015 | Schriemer et al. | |

FOREIGN PATENT DOCUMENTS

| | | |
|---|---|---|
| EP | 2 090 662 A2 | 8/2009 |
| WO | WO-2010/021752 A1 | 2/2010 |
| WO | WO-2011/097266 A1 | 8/2011 |
| WO | WO-2011/126873 A2 | 10/2011 |

OTHER PUBLICATIONS

Good NE et al. Hydrogen Ion Buffers for Biological Research. 1966. Biochemistry. vol. 5, No. 2. p. 467-477.*
U.S. Appl. No. 13/843,369, filed Mar. 15, 2013, Schriemer, David.
Amagase et al., "Acid Protease in Nepenthes," The Journal of Biochemistry, (1969), 66(4):431-439.
Athauda et al. "Enzymic and structural characterization of nepenthesin, a unique member of a novel subfamily of aspartic proteinases," Biochemical Journal (2004) 381(1):295-306.
Bennett et al., "Discovery and Characterization of the Laulimalide-Microtubule Binding Mode by Mass Shift Perturbation Mapping," Chemistry & Biology, (2010), 17:725-734.
Bethune et al., "Oral enzyme therapy for celiac sprue," Methods Enzymol., (2012), 502:241-271.
Blonder et al., "Proteomic investigation of natural killer cell microsomes using gas-phase fractionation by mass spectrometry," Biochimica et Biophysica Acta, (2004), 1698:87-95.
Chen et al., "Aspartic proteases gene family in rice: Gene structure and expression, predicted protein features and phylogenetic relation," Gene, (2009), 442:108-118.
Clabots et al., "Acquisition of Clostridium difficile by Hospitalized Patients: Evidence for Colonized New Admissions as a Source of Infection," J. Infectious Diseases, (1992), 166:561-567.
Dunker et al., "Intrinsically disordered protein," J. Molecular Graphics and Modelling, (2001), 19:26-59.
Hammel et al., "XLF Regulates Filament Architecture of the XRCC4.Ligase IV Complex," Structure, (2010), 18:1431-1442.
Hamuro et al., "Specificity of immobilized porcine pepsin in H/D exchange compatible conditions," Rapid Commun. Mass Spectrom., (2008), 22:1041-1046.
Hatano et al., "Proteomic analysis of secreted protein induced by a component of prey in pitcher fluid of the carnivorous plan *Nepenthes alata*," JPROT, (2012), 1-9.
Hatano et al., "Proteome analysis of pitcher fluid of the carnivorous plant *Nepenthes alata*," Journal of Proteome Research (2008), 7(2):809-816.
Jentsch J., "Enzymes from carnivorous plants (*Nepenthes*). Isolation of the protease nepenthacin," FEBS Letters, (1972), 21(3):273-276.
Junop et al., "Crystal structure of the Xrcc4 DNA repair protein and implications for end joining," The EMBO Journal, (2000), 19(22):5962-5970.
Kubota et al., "Stability Profiles of Nepenthesin in Urea and Guanidine Hydrochloride: Comparison with Porcine Pepsin A," Biosci. Biotechnol. Biochem., (2010), 74(11):2323-2326.
Lahdeaho et al., "Recent advances in the development of new treatment for celiac disease," Expert Opin. Biol. Ther. (Early Online) (2012), 1-12.
Mitea et al., "Efficient degradation of gluten by a prolyl endoprotease in a gastrointestinal model: implications for coeliac disease," Gut, (2008), 57:25-32.
PCT International Search Report and Written Opinion for PCT/CA2013/000970, dated Apr. 1, 2014.
Shan et al., "Structural basis for gluten intolerance in celiac sprue", Science, (2002), 297:2275-2279.
Slysz et al., "Hydra: software for tailored processing of H/D exchange daa from MS or tandem MS analyses," BMC Bioinformatics, (2009), 10:162, 1-14.
Takahashi et al., "Nepenthesin, a unique member of a novel subfamily of aspartic proteinases: Enzy matic and structural characteristics," Current Protein & Peptide Science (2005) 6(6):513-525.

(Continued)

*Primary Examiner* — Paul Holland
(74) *Attorney, Agent, or Firm* — Foley & Lardner LLP (57) ABSTRACT

Provided herein are compositions, foods comprising nepenthesin or a derivative thereof and methods of using nepenthesin or a derivative thereof for modulating gluten intolerance and related conditions, such as celiac disease.

8 Claims, 7 Drawing Sheets

(56) References Cited

OTHER PUBLICATIONS

Tokes et al., "Digestive Enzymes Secreted by the Carnivorous Plant *Nepenthes macferlanei* L.," Planta (Berl.), (1974), 119:39-46.

Vines, "On the Digestive Ferment of Nepenthes," Journal of Anatomy and Physiology, (1876) 11(Pt 1):124-127.

Warwood et al., "Guanidination chemistry for qualitative and quantitative proteomics," Rapid Commun. Mass Spectrom., (2006), 20:3245-3256.

International Preliminary Report on Patentability dated Feb. 20, 2015 for PCT/CA2013/000970, 10 pages.

Mazorra-Manzano et al., "Structure-function characterization of the recombinant aspartic proteinase A1 from Arabidopsis thaliana," Photchem., (2010), 71(5-6):515-523.

PCT International Search Report and Written Opinion dated May 26, 2014 in related PCT Patent Application No. PCT/CA2014/000258, 14 pages.

Stepniak et al., "Highly efficient gluten degradation with a newly identiifed prolyl endoprotease: implications for celiac disease," AJP Gastrointest Liver Physiol, (2006), 291:G621-G629.

Chung et al., "Aspartic Proteinases are Expressed in Pitchers of the Carnivorous Plant Nepenthes Alata Blanco," Planta, Springer Verlag, DE, vol. 214, No. 5, (Mar. 1, 2002), p. 661-667.

Kadek et al., "Expression and characterization of plant aspartic protease nepenthesin-1 from Nepenthes gracilis," Protein Expression and Purification, vol. 95, (Dec. 21, 2013), p. 121-128.

Rey et al. "Nepenthesin from Monkey Cups for Hydrogen/Deuterium Exchange Mass Spectrometry," Molecular & Cellular Proteomics, vol. 12, No. 2, (Nov. 29, 2012), p. 464-472.

Rey et al., "Addressing proteolytic efficiency in enzymatic degradation therapy for celiac disease," Scientific Reports, vol. 6, (Aug. 2, 2016) p. 30980 (entire document).

Takashai, Kenji, "Nepenthesin," Handbook of Proteolytic Enzymes, vols. 1 and 2, 3rd edition (Nov. 9, 2012), p. 125-128.

Wu Wutong, "Enzyme Pharmaceuticals" (Jan. 31, 2011), 1 page.

\* cited by examiner

TREATMENT OF GLUTEN INTOLERANCE AND RELATED CONDITIONS

CROSS-REFERENCE TO RELATED APPLICATIONS

This application claims priority under 35 U.S.C. §119(e) to U.S. Provisional Application Ser. No. 61/729,210, filed Nov. 21, 2012; and Ser. No. 61/797,040, filed Nov. 27, 2012, which are incorporated herein by reference in their entirety.

SEQUENCE LISTING

The instant application contains a Sequence Listing which has been submitted in ASCII format via EFS-Web and is hereby incorporated by reference in its entirety. Said ASCII copy, created on Jul. 18, 2014, is named 104069-0153_SL.txt and is 4000 bytes in size.

FIELD OF THE INVENTION

Provided herein are compositions, foods and methods for the treatment of gluten intolerance and related conditions, such as celiac disease.

BACKGROUND OF THE INVENTION

Ingestion of wheat, barley, rye and possibly oats, which contain gluten may cause abnormal autoimmune responses, such as celiac disease, wheat allergy and dermatitis herpetiformis, in gluten intolerant individuals. Gluten is a mixture of glutamine- and proline-rich glutenin and prolamin protein molecules. Most of the individuals having the abnormal autoimmune responses express the human leukocyte antigen (HLA) DQ2 or DQ8 molecules. The autoimmune reactions result in the development of small intestinal mucosal villous atrophy with crypt hyperplasia and mucosal inflammation. Symptoms of celiac disease can vary from individual to individual, and may include one or more of fatigue, chronic diarrhea, constipation, malabsorption of nutrients, weight loss, abdominal distension, anemia, as well as a substantially enhanced risk for the development of osteoporosis and intestinal malignancies (lymphoma and carcinoma).

Treatment for gluten intolerance commonly involves a lifelong strict gluten-free diet. However, gluten-free diet is inconvenient, restrictive, and gluten is difficult to avoid. Therefore, effective alternative treatments of gluten intolerance are needed.

SUMMARY OF THE INVENTION

This invention relates to the discovery that the enzyme nepenthesin possesses a high proteolytic activity for cleaving proteins and oligopeptides (including gluten), especially at low pH (e.g., about 2 to 3). Nepenthesin (EC 3.4.23.12) is an aspartic protease of plant origin that can be isolated or concentrated from a variety of plant sources, such as the pitcher secretions of Nepenthes, a carnivorous pitcher plant, commonly known as monkey cups in tropical regions. Tökés et al., Digestive Enzymes Secreted by the Carnivorous Plant Nepenthes macferlanei L., Planta (Berl.) 119, 39-46 (1974). It has been found that the activity of nepenthesin is about 1000 fold higher than that of that of pepsin (EC 3.4.23.1), an enzyme present in the stomach of humans partly responsible for degrading food proteins into peptides. It has also been found that nepenthesin has a much more relaxed specificity than pepsin, efficiently cleaving after most amino acid residues with the exception of G, S, T, V, I and W. Notably, it cleaves at after K, R and P. By comparison, pepsin presents high-efficiency cleavage for the hydrophobic residues F, L and M but cleavage after P, H, K and R is essentially forbidden.

Gluten intolerance and associated conditions and symptoms, such as celiac disease and/or dermatitis herpetiformis, are caused by the patient's abnormal immune response to gluten in the small intestinal mucosa. Certain gluten components are resistant to cleavage by gastric and pancreatic peptidases such as pepsin, trypsin, chymotrypsin, and the like. While not wishing to be bound by any theories, it is contemplated that degradation of gluten to non-toxic peptides by nepenthesin prior to arriving at the intestinal tract of a patient decreases the levels of toxic gluten proteins or peptides going into the small intestine. As nepenthesin is acid stable, it is compatible with the stomach pH and digests gluten so as to modulate a patient's gluten intolerance or related conditions or symptoms.

Given its high activity at low pH and its broad spectrum of activity, nepenthesin is especially useful in digesting gluten proteins in the stomach. The degradation of gluten to non-toxic peptides is also referred to as detoxification of gluten.

In one aspect, provided are methods for modulating gluten intolerance in a patient with gluten intolerance, which method comprises administering an effective amount of nepenthesin or a derivative thereof to said patient.

In one embodiment, nepenthesin or a derivative thereof is administered as a food additive such that nepenthesin or the derivative thereof is combined with gluten containing food to modulate or inhibit conditions associated with gluten intolerance. Nepenthesin or a derivative thereof can be used alone or in combination with such food.

In another aspect, provided are methods for modulating a condition mediated by gluten intolerance in a patient which method comprises administering an effective amount of nepenthesin or a derivative thereof to said patient. Such conditions include by way of example only celiac disease, wheat allergy, gluten sensitivity and/or dermatitis herpetiformis.

In any event, nepenthesin or a derivative thereof can be administered to the patient prior to, concurrently with, or shortly after consumption of a food comprising gluten or suspected of comprising gluten.

In another aspect, provided are methods for modulating gluten intolerance or an associated condition, such as celiac disease, wheat allergy, gluten sensitivity or dermatitis herpetiformis, in a patient in need thereof, comprising treating a food comprising gluten or suspected of comprising gluten with an effective amount of nepenthesin prior to consumption by the patient.

In another aspect, provided are foods or compositions comprising nepenthesin.

These and other aspects of the invention will be further described in the text that follows.

DETAILED DESCRIPTION

I. Definitions

Unless defined otherwise, all technical and scientific terms used herein have the same meanings as commonly understood by one of ordinary skill in the art to which this invention belongs. Although any methods and materials similar or equivalent to those described herein can be used in the practice or testing of the present invention, the preferred methods, devices, and materials are now described. All technical and patent publications cited herein are incorporated herein by reference in their entirety. Nothing herein is to be construed as an admission that the invention is not entitled to antedate such disclosure by virtue of prior invention.

As used in the specification and claims, the singular form "a", "an" and "the" include plural references unless the context clearly dictates otherwise.

As used herein, the term "comprising" is intended to mean that the compositions and methods include the recited elements, but not excluding others. "Consisting essentially of" when used to define compositions and methods, shall mean excluding other elements of any essential significance to the combination. For example, a composition consisting essentially of the elements as defined herein would not exclude other elements that do not materially affect the basic and novel characteristic(s) of the claimed invention. "Consisting of" shall mean excluding more than trace amount of other ingredients and substantial method steps recited. Embodiments defined by each of these transition terms are within the scope of this invention.

As used herein, the term "gluten" generally refers to the proteins present in wheat or related grain species, including barley and rye, which have potential harmful effect to certain individuals. Gluten proteins include gliadins such as α-gliadins, β-gliadins, γ-gliadins and ω-gliadins, which are monomeric proteins, and glutenins which are highly heterogeneous mixture of aggregates of high molecular weight and low-molecular-weight subunits held together by disulphide bonds. Many wheat gluten proteins have been characterized, see, for example, Woychik et al., Amino Acid Composition of Proteins in Wheat Gluten, *J. Agric. Food Chem.*, 9(4), 307-310 (1961). The term gluten as used herein also includes oligopeptides that can be derived from normal human digestion of gluten proteins from gluten containing foods and cause the abnormal immune response. Some of these oligopeptides are resistant to normal digestive enzymes. Gluten, including the above-mentioned proteins and oligopeptides, is believed to act as antigens for T cells in celiac sprue in patients with gluten intolerance.

The term "nepenthesin" refers to the aspartic protease having the Enzyme Commission number EC 3.4.23.12, and includes all isoforms and variants of nepenthesin such as nepenthesin I and nepenthesin II, and salts thereof. Salts refer to those salts formed by nepenthesin with one or more base or one or more acid which retain the biological effectiveness and properties of the free nepenthesin, and which are not biologically or otherwise undesirable. Salts derived from inorganic bases include, but are not limited to, the sodium, potassium, lithium, ammonium, calcium, magnesium, iron, zinc, copper, manganese, aluminum salts and the like. Salts derived from organic bases include, but are not limited to, salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, 2-dimethylaminoethanol, 2-diethylaminoethanol, dicyclohexylamine, lysine, arginine, histidine, caffeine, procaine, hydrabamine, choline, betaine, ethylenediamine, glucosamine, methylglucamine, theobromine, purines, piperazine, piperidine, N-ethylpiperidine, polyamine resins and the like. Acids that can form salts include, but are not limited to, inorganic acids such as hydrochloric acid, hydrobromic acid, sulfuric acid, nitric acid, phosphoric acid and the like, and organic acids such as acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicyclic acid and the like.

Nepenthesin derivatives include biological equivalents, fragments and extended nepenthesin, and salts thereof, that retain the ability to detoxify the gluten. In some embodiments, nepenthesin derivatives include biological equivalents of nepenthesin. "Biological equivalents" include those having at least about 80% homology or identity or alternatively, at least about 85%, or alternatively at least about 90%, or alternatively at least about 95%, or alternatively 98% homology with nepenthesin, or alternatively a polypeptide or protein encoded by a polynucleotide that hybridizes under stringent conditions to the nucleotide sequence encoding nepenthesin or its complement, while maintaining the desired structure and exhibiting at least part of the proteolytic activity of nepenthesin.

In some embodiments, the nepenthesin derivative is a fragment of nepenthesin having at least about 20 contiguous amino acids of the full nepenthesin protein, or at least about 50 contiguous amino acids, or comprising 100 or more contiguous amino acids, up to the complete protein of nepenthesin. Nepenthesin derivatives also include nepenthesin having additional sequences.

In some embodiments, a nepenthesin derivative has at least about 10% of the proteolytic activity of nepenthesin, or at least about 50%, or at least about 70%, or at least about 90% of the proteolytic activity of nepenthesin or 100% or more of the proteolytic activity of nepenthesin.

"Hybridization" refers to hybridization reactions that can be performed under conditions of different "stringency". Conditions that increase the stringency of a hybridization reaction are widely known and published in the art: see, for example, Sambrook and Russell eds. (2001) Molecular Cloning: A Laboratory Manual, 3rd edition. Examples of relevant conditions include (in order of increasing stringency): incubation temperatures of 25° C., 37° C., 50° C., and 68° C.; buffer concentrations of 10×SSC, 6×SSC, 1×SSC, 0.1×SSC (where SSC is 0.15 M NaCl and 15 mM citrate buffer) and their equivalent using other buffer systems; formamide concentrations of 0%, 25%, 50%, and 75%; incubation times from 5 minutes to 24 hours and washes of increasing duration, increasing frequency, or decreasing buffer concentrations.

The term "modulate" or "modulating" means any treatment of a disease or disorder in a subject, such as a mammal, including:
  preventing or protecting against the disease or disorder, that is, causing the abnormal biological reaction or symptoms not to develop;
  inhibiting the disease or disorder, that is, arresting or suppressing the development of abnormal biological reactions and/or clinical symptoms; and/or
  relieving the disease or disorder that is, causing the regression of abnormal biological reactions and/or clinical symptoms.

As used herein, the term "preventing" refers to the prophylactic treatment of a patient in need thereof. The prophylactic treatment can be accomplished by providing an appropriate dose of a therapeutic agent to a subject at risk of suffering from an ailment, thereby substantially averting onset of the ailment.

As used herein, the term "condition" refers to a disease state for which the compounds, compositions and methods provided herein are being used.

As used herein, the term "patient" or "subject" refers to mammals and includes humans and non-human mammals. In particular embodiments herein, the patient or subject is a human.

The term "about" when used before a numerical value indicates that the value may vary within a reasonable range, such as ±5%, ±1%, and ±0.2%.

II. Methods and Compositions

In one aspect, provided are methods for modulating gluten intolerance in a patient with gluten intolerance which method comprises administering an effective amount of nepenthesin or a derivative thereof to said patient.

In one embodiment, nepenthesin or a derivative thereof is administered as a food additive such that nepenthesin or a derivative thereof is combined with gluten containing food to modulate or inhibit conditions associated with gluten intolerance. Nepenthesin or a derivative thereof can be used alone or in combination with such food.

In another aspect, provided are methods for modulating a condition mediated by gluten intolerance in a patient which method comprises administering an effective amount of nepenthesin or a derivative thereof to said patient. Such conditions include by way of example only celiac disease, wheat allergy, gluten sensitivity and dermatitis herpetiformis. Nepenthesin or a derivative thereof can be administered to the patient prior to, concurrently with, or shortly after ingestion of a food comprising gluten or suspected of comprising gluten.

Nepenthesin has two known isoforms: nepenthesin I (known to have two variants nepenthesin Ia and nepenthesin Ib) and II. The sequences of nepenthesin and the nucleotide sequencing of the cDNA encoding nepenthesin are known in the art, for example, described in Athauda S B et al., Enzymic and structural characterization of nepenthesin, a unique member of a novel subfamily of aspartic proteinases, *Biochem. J.* 381:295-306 (2004).

Nepenthesin can be concentrated or purified by known methods, such as filtration or affinity purification based on immobilized pepstatin, from a natural source, such as pitcher secretions of plants such as Nepenthes. Besides being isolated from a plant source, nepenthesin or a derivative thereof may be prepared by chemical synthesis or biosynthesis, using conventional methods as known in the art. Chemical synthesis can be achieved by coupling of the amino acids according to the sequence of nepenthesin. Various peptide coupling methods and commercial peptide synthetic apparatuses are available to synthesis peptide or proteins, for example, automated synthesizers by Applied Biosystems, Inc., Foster City, Calif., Beckman, and other manufacturers. Biosynthesis of nepenthesin can be achieved using recombinant production systems by transcribing a cell with the DNA and/or messenger RNA of nepenthesin with known bioengineering technologies so that the cell is capable of producing nepenthesin. For example, nepenthesin can be produced by establishing host-vector systems in organisms such as *Escherichia coli, Saccharomyces cerevisiae, Pichia pastoris, Lactobacillus,* Bacilli, Aspergilli, and plant cell cultures, such as tobacco cells, etc.

The synthetic nepenthesin or a derivative thereof can be concentrated or purified according to known methods, such as those for isolating nepenthesin or a derivative thereof from the plant pitcher liquid.

In some embodiments, the protein product isolated from a natural source or a synthetic source comprises at least 20% by weight of nepenthesin or a derivative thereof. In some embodiments, the isolated protein product comprises at least about 50%, about 75%, about 90%, about 95% by weight of nepenthesin or a derivative thereof. In some embodiments, the isolated protein product comprises at least 99% by weight of nepenthesin or a derivative thereof.

In some embodiments, nepenthesin or a derivative thereof is administered to the patient prior to ingestion by the patient of the food comprising gluten or suspect of comprising gluten. In some embodiments, nepenthesin or a derivative thereof is administered within a period that nepenthesin or the derivative thereof is at least partially effective (for example, at least about 10%, 20%, 50%, 70%, 90% of original activity) in degrading gluten in the food that the patient will ingest. In some embodiments, nepenthesin or a derivative thereof is administered not more than about 4 hours, 3 hours, 2 hours, 1 hour, or 30 minutes prior to ingestion of the food by the patient.

In some embodiments, nepenthesin or a derivative thereof is administered to the patient concurrently with ingestion by the patient of the food comprising gluten or suspect of comprising gluten. In some embodiments, nepenthesin or a derivative thereof is administered with the food, such as an ingredient or additive to the food. In some embodiments, nepenthesin or a derivative thereof is administered separately from the food.

In some embodiments, nepenthesin or a derivative thereof is administered to the patient shortly after ingestion by the patient of the food comprising gluten or suspect of comprising gluten. In some embodiments, nepenthesin or a derivative thereof is administered within a period that at least part (for example, at least about 10%, 20%, 50%, 70%, 90%) of the gluten in the food is still in the stomach of the patient. In some embodiments, nepenthesin or a derivative thereof is administered not more than 4 hours, 3 hours, 2 hours, 1 hour, or 30 minutes after ingestion of the food by the patient.

Nepenthesin or a derivative thereof can be administered in a variety of compositions alone or with appropriate, pharmaceutically acceptable carriers or diluents or dietary ingredients.

Accordingly, in another aspect, provided herein is an edible composition comprising nepenthesin or a derivative thereof. In some embodiments, the composition is a dietary supplement. In some embodiments, the composition is a pharmaceutical composition. In some embodiments, the composition is a food or food additive. The compositions may be formulated into solid, semi-solid, or liquid forms, such as tablets, capsules, powders, granules, ointments, solutions, injections, gels, and microspheres. Administration of nepenthesin or a derivative thereof can be achieved in various ways, for example, by oral administration.

For oral administration, nepenthesin or a derivative thereof can be used alone or in combination with appropriate additives to make tablets, powders, granules, capsules, syrups, liquids, suspensions, etc. For example, solid oral forms of nepenthesin or a derivative thereof can be prepared with conventional additives, disintegrators, lubricants, diluents, buffering agents, moistening agents, preservatives and flavoring agents. Non-limiting examples of excipients include lactose, mannitol, corn starch, potato starch, crystalline cellulose, cellulose derivatives, acacia, corn starch, sodium carboxymethylcellulose, talc, magnesium stearate, flavors and colors. In some embodiments, the formulation releases nepenthesin or a derivative thereof in the stomach of the patient so that gluten can be degraded by the nepenthesin or derivative thereof.

Nepenthesin or a derivative thereof can be lyophilized from an aqueous solution optionally in the presence of appropriate buffers (e.g. phosphate, citrate, histidine, imidazole buffers) and excipients (e.g. cryoprotectants such as sucrose, lactose, trehalose). Lyophilized cakes can optionally be blended with excipients and made into different forms.

In some embodiments, nepenthesin or a derivative thereof is administered as a food additive together with a food comprising gluten or suspected of comprising gluten, such as bread, pasta, cereal, and the like, made from wheat, rye and barley, etc. In some embodiments, nepenthesin or a derivative thereof is added as an ingredient in such food. In some embodiments, nepenthesin or a derivative thereof is dispersed into a food prior to consumption, optionally at a pH where it is inactive, such as a pH of about or above 5. In some embodiments, nepenthesin or a derivative thereof can be made or incorporated into a powder, a spread, a spray, a sauce, a dip, a whipped cream, etc., that can be applied to the gluten comprising food when the food is being consumed by a patient. In some embodiments, nepenthesin or a derivative thereof can be made into forms that appeal to one's appetite, such as candies, chewing gums, dietary supplement chews, syrup, etc. for easy administration. In some embodiments, nepenthesin or a derivative thereof can be mixed with common food items, such as sugar, salt, salad dressing, spices, cheese, butter, margarines, spreads, butter, frying shortenings, mayonnaises, dairy products, nut butters, seed butters, kernel butters, peanut butter, etc. Preferably, the food items or additives comprising nepenthesin do not require heating before being ingested by a patient so that possible loss of activity of nepenthesin or a derivative thereof due to elevated temperature can be minimized.

Typically, nepenthesin or a derivative thereof is administered in an amount that is safe and sufficient to produce the desired effect of gluten detoxification. The exact amount depends on many factors, such as the particular nepenthesin or derivative thereof administered, and the amount and type of food, the patient's sensitivity to gluten, etc. Generally, nepenthesin or a derivative thereof is administered when needed, such as when the patient will be or is consuming or has consumed a food comprising gluten or suspected of comprising gluten. It can be administered in dosages of about 0.01 mg to about 1000 mg/kg body weight per day, or about 1 mg to about 100 g per dose for an average person. In some embodiments, nepenthesin or a derivative thereof can be administered at 0.01, 0.1, 1, 5, 10, 50, 100, 500, or 1000 mg/kg body weight per day, and ranges between any two of these values (including endpoints). In some embodiments, nepenthesin or a derivative thereof can be administered at 1 mg, 10 mg, 100 mg, 200 mg, 500 mg, 700 mg, 1 g, 10 g, 20 g, 50 g, 70 g, 100 g per dose, and ranges between any two of these values (including endpoints). In some embodiments, it may be administered once, twice, three times, etc. a day, depending on the number of times the patient ingests a gluten containing food.

In some embodiments, nepenthesin or a derivative thereof is administered with another enzyme, such as a gastric protease (e.g., pepsin and pepsinogen), another aspartic protease, such as those described by Chen et al., Aspartic proteases gene family in rice: Gene structure and expression, predicted protein features and phylogenetic relation, *Gene* 442:108-118 (2009), and enzymes such as prolyl endopeptidase (PEP), dipeptidyl peptidase IV (DPP IV), and dipeptidyl carboxypeptidase (DCP) or cysteine proteinase B described in U.S. Pat. No. 7,910,541.

In some embodiments, nepenthesin is administered to the patient with another agent. Non-limiting examples of agents that can be administered with nepenthesin include inhibitors of tissue transglutaminase, anti-inflammatory agents such as HMG-CoA reductase inhibitors (e.g., compactin, lovastatin, simvastatin, pravastatin and atorvastatin), leukotriene receptor antagonists (e.g., montelukast and zafirlukast), COX-2 inhibitors (e.g., celecoxib and rofecoxib), p38 MAP kinase inhibitors (e.g., BIRB-796); mast cell-stabilizing agents such as sodium chromoglycate (chromolyn), pemirolast, proxicromil, repirinast, doxantrazole, amlexanox nedocromil and probicromil, anti-ulcer agents, anti-allergy agents such as anti-histamine agents (e.g., acrivastine, cetirizine, desloratadine, ebastine, fexofenadine, levocetirizine, loratadine and mizolastine), inhibitors of transglutaminase 2 (TG2), and anti-TNFα agents.

In another aspect, provided are methods for treating gluten intolerance or an associated condition, such as celiac disease, wheat allergy, gluten sensitivity and dermatitis herpetiformis, in a patient in need thereof, comprising treating a food comprising gluten or suspected of comprising gluten with an effective amount of nepenthesin or a derivative thereof prior to consumption by the patient. In some embodiments, the food is combined with an effective amount of nepenthesin or a derivative thereof during its preparation, preferably after any heating steps.

In another aspect, provided is a food product comprising nepenthesin or a derivative thereof. In some embodiments, the food product comprises gluten or is suspected of comprising gluten, such as bakery products (e.g., cakes, muffins, donuts, pastries, rolls, and bread), pasta, crackers, tortilla chips, cereal etc. made from wheat, rye and barley. In some embodiments, the food product can be consumed with another food product comprising gluten or suspected of comprising gluten. Non-limiting examples of such food include a powder, a spread, a spray, a sauce, a dip, a whipped cream, candies, chewing gums, syrup, sugar, salt, salad dressing, spices, cheese, butter, margarines, spreads, butter, frying shortenings, mayonnaises, dairy products, nut butters, seed butters, kernel butters, peanut butter, etc.

In some embodiments, the nepenthesin or derivative thereof is admixed with food, or used to pre-treat foodstuffs containing glutens. Nepenthesin present in foods can be enzymatically active to reduce the level of gluten in the food prior to or during ingestion.

III. Examples

Unless stated otherwise, the abbreviations used throughout the specification have the following meanings:

g=gram
kDa=kiloDalton
kg=kilogram
L=liter
LC=liquid chromatography
mg=milligram
min=minute
mL=milliliter
mM=millimolar
MS=mass spectrometry
nM=nanomolar
pM=picomolar
s.d.=standard deviation
µCi=microcurie
µL=microliter
µM=micromolar
µm=micrometer
° C.=degree Celsius These one-letter symbols have the following meaning when representing amino acids:

A=alanine
R=Arginine
N=Asparagine
D=Aspartic acid
C=Cysteine
E=Glutamic acid
Q=Glutamine
G=Glycine
H=Histidine
I=Isoleucine
L=Leucine
K=Lysine
M=Methionine
F=Phenylalanine
P=Proline
S=Serine
T=Threonine
W=Tryptophan
Y=Tyrosine
V=Valine Materials and Methods Chemicals Water and acetonitrile, HPLC grade form Burdick and Jackson, were purchased from VWR. Formic acid, Tris, glycine were purchased from Sigma Aldrich.

Plant Culture

Transplants of *Nepenthes rafflesiana, Nepenthes ampularia, Nepenthes mirabilis,* and *Nepenthes globosa* were purchased from Keehns Carnivores (accessible via hypertext transfer protocol on the world wide web at keehnscarnivores.ca). These were potted with wood bark, perlite, peat moss and humus (40, 35, 10, 5% respectively). Growth conditions involved 14 hours of light per day, 80% humidity and temperature in the 23-28 oC range with 2 to 3 waterings a week. Upon pitcher maturity, plants were fed with one or two *Drosophila* per pitcher and the pitcher fluid harvested one week later. Pitchers and their secretions were left to recover for one week prior to a second round of feeding and extraction.

Fluid Preparation

Pitcher fluid was collected from all four species of plants and combined. The crude pitcher fluid was first clarified through a 0.22 µm filter, then concentrated 80 to 100 fold using an Amicon Ultra centrifugal 10 kDa molecular weight cut-off filter (both from Millipore). Prior to use in digestions, the concentrate was acid-activated with 100 mM Glycine HCl (pH 2.5) for 3 hours, then washed 3× with 100 mM Glycine-HCl (pH 2.5) in the filtration device, using 10× fluid volume for each wash). The final isolate was then rediluted to an 11× concentration based on the original sampling of pitcher fluid.

Nepenthesin Digest Mapping by Mass Spectrometry

Digestions of proteins were carried out in solution using a LEAP HTX-PAL autosampler and dispensing system designed for hydrogen/deuterium exchange (HDX) applications, and data were collected with an AB Sciex Triple-TOF 5600 QqTOF mass spectrometer. Peptides were identified using Mascot (v2.3) from MS/MS data. Briefly, 8 µL of 8 µM protein (XRCC4, XLF, Ligase IV-tandem BRCT domains, PNK, myoglobin, or cytochrome C) were mixed with 10 µA of 11× concentrated fluid for 2 min. at 10° C. Myoglobin and cytochrome C were purchased from Sigma. After dilution to 1 µM substrate concentration, 15 µA were injected into the chilled reversed-phase LC system (4° C.) connected to the mass spectrometer. The peptides were trapped on a 5 cm, 200 µm i.d. Onyx C18 monolithic column (Phenomenex Inc.) and eluted with an acetonitrile gradient from 3% to 40% in 10 minutes. Peptides detected in these analyses were selected for CID fragmentation in multiple information-dependent acquisitions of MS/MS spectra, akin to the gas-phase fractionation strategy. Blonder J, et al., Proteomic investigation of natural killer cell microsomes using gas-phase fractionation by mass spectrometry. *Biochimica Et Biophysica Acta-Proteins and Proteomics* 1698 (1):87-95 (2004). Spectra were searched against a miniature database containing the sequences for all six proteins. Sequencing results were manually verified.

HD Exchange of a Complex Involved in DNA-Damage Repair

Stock solutions of XRCC4 (1-200) with BRCT, and XRCC4 (full length) with BRCT were diluted in buffer (10 mN Tris-HCl, pH 7.5) to equimolar concentrations (10 mM) and incubated at 4° C. for a minimum of 30 min to promote complexation. The samples were held at 4° C. until HDX analysis. Aliquots were deuterated for 2 min at 20° C. with the addition of D$_2$O (25% v/v). Aliquots were then digested in two ways. In the first digestion strategy, protein deuteration was quenched by adding the sample to chilled 100 mM glycine-HCl (pH 2.5), and the quenched protein solution was injected into a pepsin microreactor. This microreactor was installed in the HTX-PAL system between the injector valve and the C18 column. Protein digest was captured on the monolithic C18 capillary column and eluted into the mass spectrometer. All fluidic elements, including the microreactor, were chilled at 4° C. to minimize deuterium back-exchange during the analysis time (<15 min). In the second digestion strategy, an equivalent amount of deuterated protein was simultaneously quenched and digested with 3 or 5 µA of 11× nepenthes fluid for 3 or 5 min, respectively, at 10° C. The sample was injected into the chilled LC-system connected to the mass spectrometer.

Replicate mass shift measurements were made (4 or more) and referenced to control protein states—free XRCC4 (1-200), free XRCC4 (full length) and free LigIV-BRCT. The average deuterium level for each peptide was determined using Mass Spec Studio (manuscript in preparation), which is a rebuild of Hydra v1.5. Slysz G W, et al., Hydra: software for tailored processing of H/D exchange data from MS or tandem MS analyses. *Bmc Bioinformatics* 10 (2009). Perturbations in mass shifts were considered significant if (a) they passed a two-tailed t test (p<0.05) using pooled standard deviations from the analyses of each state, (b) they passed a distribution analysis to guard against spectral overlap and (c) they exceeded a threshold shift value (±2 s.d.) based on a measurement of the shift noise and assuming its normal distribution Bennett M J, et al., Discovery and Characterization of the Laulimalide-Microtubule Binding Mode by Mass Shift Perturbation Mapping. *Chemistry & Biology* 17(7):725-734 (2010).

Results

Pitcher Fluid Extract

The fluidic secretions of the pitcher plant were concentrated and the digestion enzymes activated by pH reduction (pH 2.5). The impact of the enrichment process and the activation on the fluid proteome was determined using proteomics methods. First, to confirm the presence of nepenthesin enzyme, the inactive concentrate was separated by SDS-PAGE. Seven contiguous gel zones with very faint coomassie staining were digested with trypsin and analysed by nanoLC-MS/MS using standard methods. This is not expected to be a complete catalog of the activated fluid proteome, but the analysis confirmed the presence of the aspartic protease nepenthesin I/II, as well as a glucanase, chitinase, carboxypeptidase and peroxidase of plant origin, plus modest levels of *drosophila* and bacterial contamination. The low complexity of the fluid proteome is consistent with recent analyses, Hatano N, Hamada T (2012) Proteomic analysis of secreted protein induced by a component of prey in pitcher fluid of the carnivorous plant *Nepenthes alata*. *Journal of Proteomics* 3; 75(15):4844-52 (Epub Jun. 15, 2012), but nepenthesin-I was found distributed over a much wider mass range in this analysis (40-70 kDa). The acid-activated fluid was then processed and analyzed in a similar fashion. The activation process reduced the overall protein yield, and also appeared to simplify the composition. Aside from nepenthesin-I, only minor contamination from keratin and actin were in evidence. These analyses point to the low complexity of the enriched fluid, where nepenthesin is the major component. The total protein concentration of the activated and 80× enriched fluid was measured by a BCA assay to be 22 ng/µL. This value is consistent with an earlier study describing enrichment of the fluid. Tokes Z A, et al., Digestive Enzymes Secreted by Carnivorous Plant Nepenthes-Macferlanei-L. *Planta* 119(1):39-46 (1974).

A series of proteins were digested with the enriched fluid under conditions suitable for HDX-MS experiments. The digestion specificity of the concentrate was characterized at the P1 and P1' positions (FIG. 1), to support a comparison with similar studies applied to pepsin. Hamuro Y, et al., Specificity of immobilized porcine pepsin in H/D exchange compatible conditions. *Rapid Communications in Mass Spectrometry* 22(7):1041-1046 (2008). In this example, the enzyme-to-substrate ratio was 1:85 based on the assumption that all the measured protein in the enriched fluid is nepenthesin, even though some contaminating proteins were obviously present.

Figure 1:
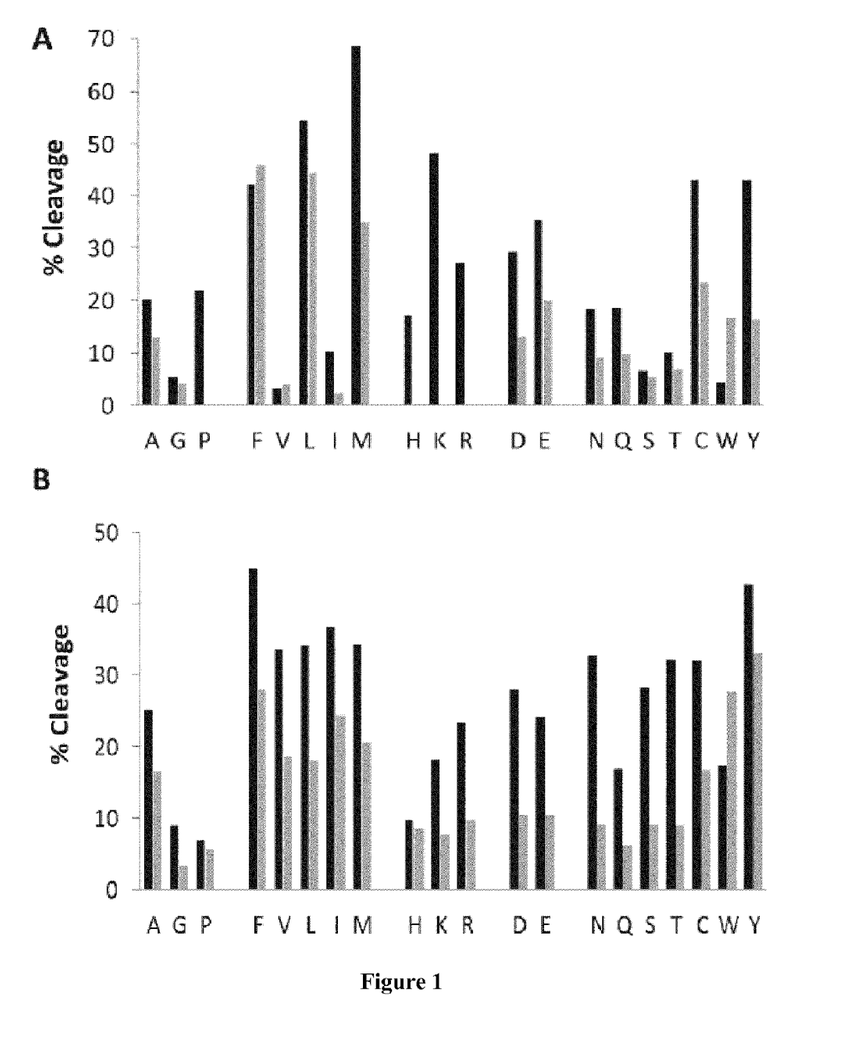
FIG. 1 shows nepenthesin cleavage preferences at (A) the P1 or N-terminal side of the cleavage site and at (B) the P1' or C-terminal side of the cleavage site. Data is grouped according to amino acid type and compared to a similar rendering of pepsin data from Hamuro et al. Specificity of immobilized porcine pepsin in H/D exchange compatible conditions. *Rapid Communications in Mass Spectrometry* 22(7):1041-1046 (2008). Black bars indicate nepenthesin digestion and the grey bars pepsin digestion. The % cleavage represents the number of observed cleavages at the given residue, relative to the total number of the given residues in the set. Nepenthesin data were obtained from digests of six denatured proteins, as described in the Example.

The nepenthesin data represents an assessment of 1612 residues and although not as extensive as the corresponding pepsin data (13,766 residues), the sequence diversity is sufficiently high in the protein set to warrant a comparison at the level of P1 and P1' positions. The greatest specificity for pepsin appears to be in the P1 position. It presents high-efficiency cleavage for the hydrophobic residues F, L and M but cleavage after P, H, K and R is essentially forbidden. Nepenthesin cleaves after most residues with the exception of G, S, T, V, I and W. It supports a high rate of cleavage after the expected pepsin P1 residues but also at the residues forbidden in pepsin digestion, notably K, R and P. In the P1' position, pepsin shows a preference for hydrophobic residues in general, including any residue with aromaticity. Conversely, nepenthesin demonstrates little in the way of selectivity at the P1' position, except perhaps against G, P and H. Overall, nepenthesin demonstrates significantly relaxed specificity at the P1 position relative to pepsin, and provides an indication of very high efficiency.

Figure 2:
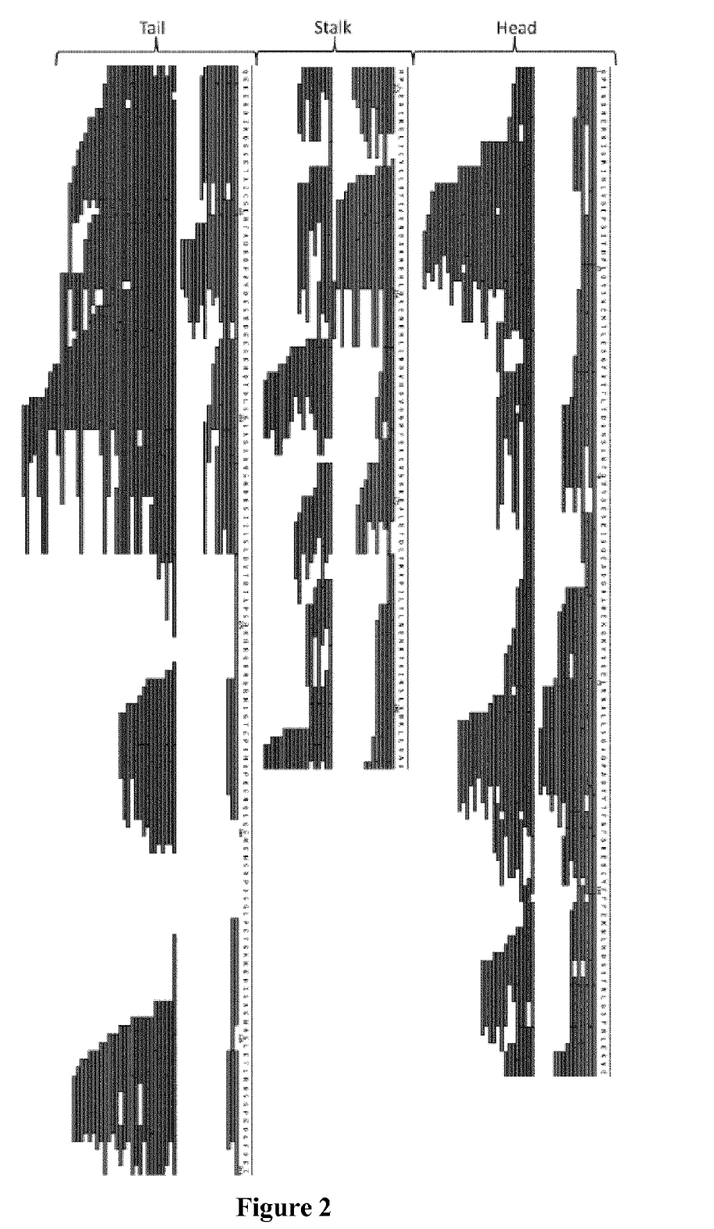
FIG. 2 shows an XRCC4 (SEQ ID NO: 1) composite peptide sequence map, arranged according to domain type. The peptides were obtained using pepsin digestion at four different enzyme:substrate ratios (65:1 to 520:1, light gray/top set of bars), and using nepenthesin digestion at four different enzyme:substrate ratios (0.0075:1 to 0.38:1, dark gray/bottom set of bars).

To determine if relaxed specificity translates into an improvement in sequence mapping for HDX-MS applications, full-length XRCC4, a protein that contains a globular domain, and extended helical stalk, and a long disordered C-terminal was profiled. Hammel M, et al., XLF Regulates Filament Architecture of the XRCC4. Ligase IV Complex. *Structure* 18(11):1431-1442 (2010); and Junop M S, et al., Crystal structure of the Xrcc4 DNA repair protein and implications for end joining *Embo J* 19(22):5962-5970 (2000). Such multi-domain proteins are challenging to encompass in a single digestion protocol, and in particular, intrinsically-disordered regions tend to digest poorly with pepsin as they are relatively depleted in hydrophobic residues and enriched in proline and charged residues. Dunker A K, et al. Intrinsically disordered protein. *Journal of Molecular Graphics & Modelling* 19(1):26-59 (2001). The pepsin and nepenthesin maps for this protein are displayed in FIG. 2. In this comparison, an exhaustive mapping was pursued for both enzymes, using a range of different protease amounts, and recursive MS/MS experiments. Nepenthesin provides superior coverage of the full length protein: 357 peptides for nepenthesin compared to 187 for pepsin. (The average peptide length of 11 residues was the same for both enzymes.) Both enzymes represent the globular and stalk regions with a large number of overlapping peptides but the complementarity provided by nepenthesin is evident. For example, nepenthesin offers considerably deeper coverage of a β-sheet region in the globular domain (residues 1-30). The disordered C-terminal region is covered to a much greater extent as well, and to a considerably higher level of redundancy. Each residue in this disordered tail region receives 16× coverage using nepenthesin and only 4.7× coverage with pepsin.

Figure 3:
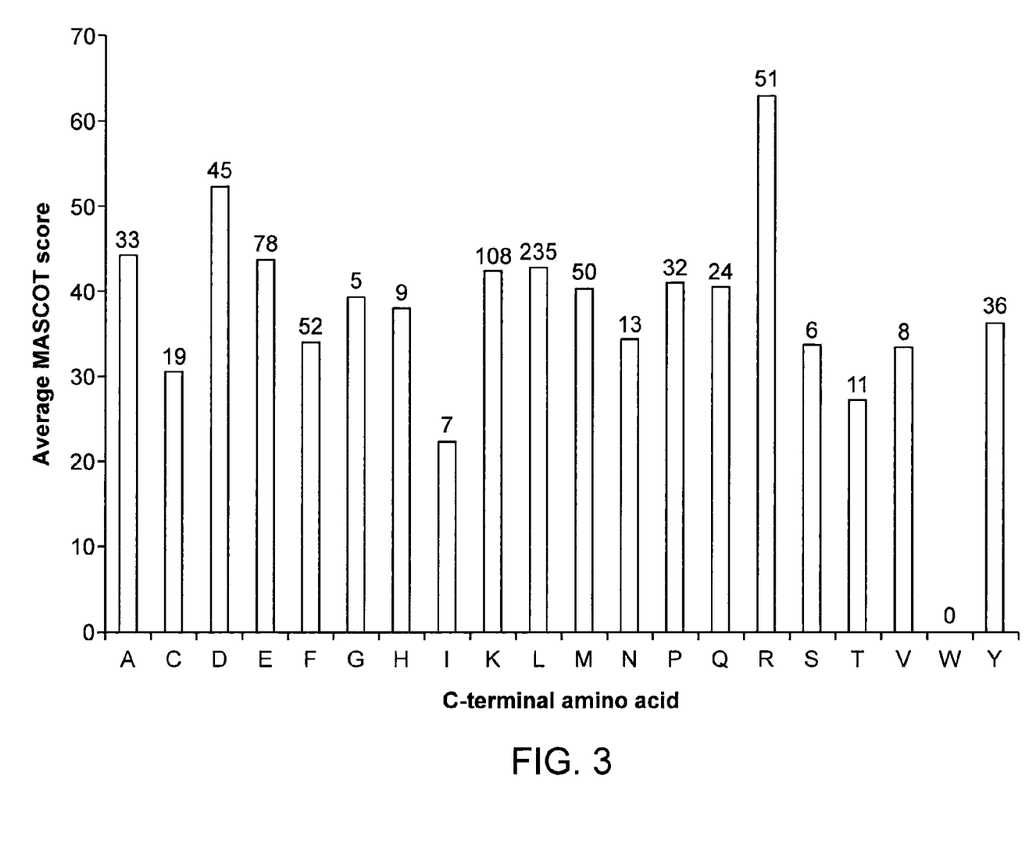
FIG. 3 shows the average MASCOT score of peptides obtained after nepenthesin digestion, grouped by C-terminal amino acid. The number of peptides used for each calculation is associated with the terminal amino acid, above the bar. Peptides were obtained from the digests of six denatured proteins, as described in the Example.

The existence of any bias in peptide detection is explored by selecting average search score as the metric (FIG. 3). The approach emphasizes confidence in sequence identification as the principle means by which sequence maps are defined. One outliner is R. The higher scores for peptides terminating in R likely reflect a combination of higher average peptide intensity and better fragmentation, which is consistent with what we know from trypsin-based bottom-up proteomics. Warwood S, et al. Guanidination chemistry for qualitative and quantitative proteomics. *Rapid Communications in Mass Spectrometry* 20(21):3245-3256 (2006).

Figure 4:
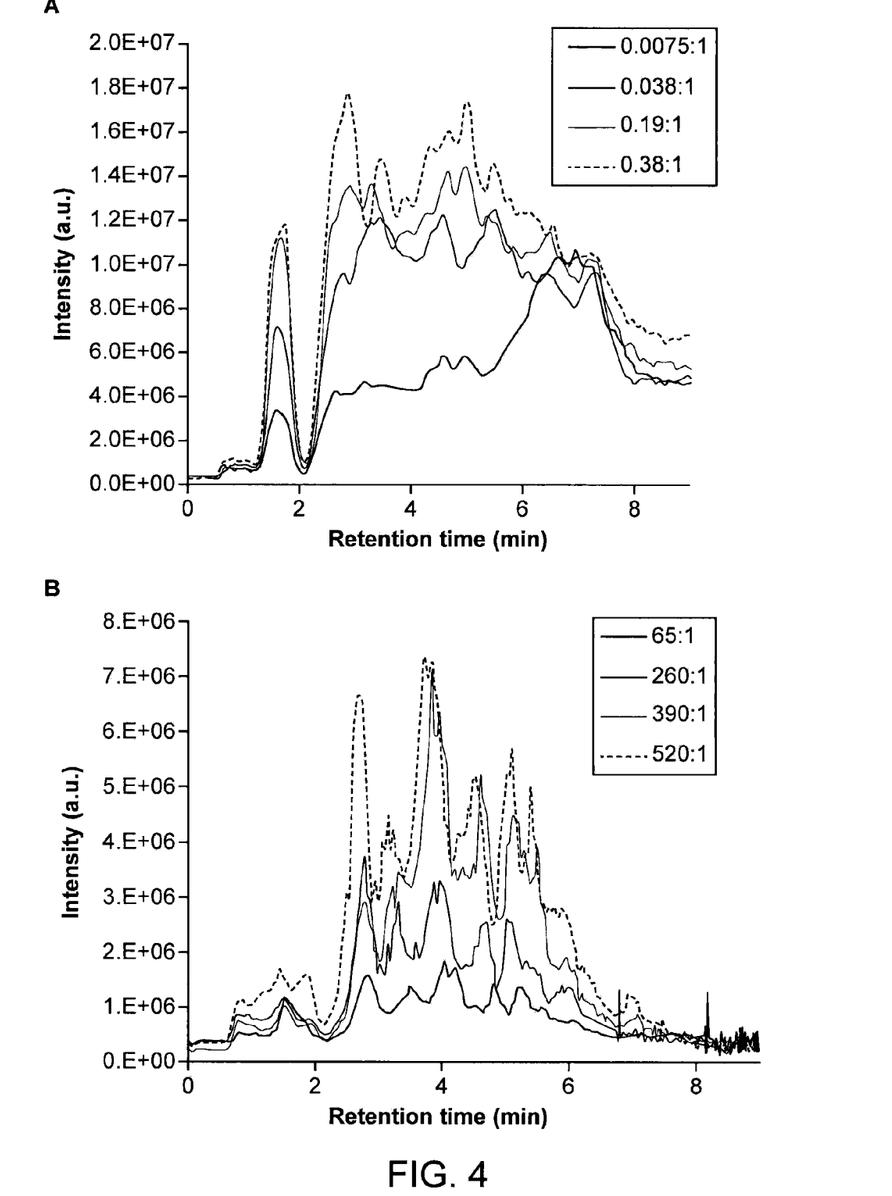
FIG. 4 shows peptide ion chromatograms (PICs) of XRCC4 digested with (A) nepenthesin and (B) pepsin over a range of enzyme:substrate ratios (shown in the legend). PICs for enzymatic digestion were generated from the same mass-load of substrate on column.

The enzyme efficiency was examined in greater detail. The degree to which the peptide mass map could be varied, or tuned, simply by altering the enzyme-to-substrate ratio is shown in FIG. 4. Nepenthesin load was varied over a 50-fold range for in-solution digestions. For the pepsin experiment, immobilized pepsin in a slurry format was used rather than free pepsin to avoid extensive pepsin autolysis. The enzyme load was varied over an 8-fold range; lower amounts led to poor peptide intensities and higher amounts had no effect on the map. It was found that nepenthesin generated a very low autolysis profile even at the higher loads. An aggregate peptide ion chromatogram (PIC) was used as a measure of effective digestion. The comparison of the relatively similar distributions found at 0.38:1 (nepenthesin:substrate) with 520:1 (pepsin:substrate) represents a remarkable 1400-fold improvement in efficiency for nepenthesin over pepsin in HDX-like applications.

The nepenthesin digest could be more readily tuned from large fragments to small by varying the enzyme load, and generating a variable representation of XRCC4. This is demonstrated in FIG. 4A by the transition in the PIC from long retention times at low load to short retention times at high load. This transition correlated with the average peptide length for the most abundant peptides shifting from >12 at low enzyme load to 10 at high enzyme load. Conversely, varying pepsin load did not significantly alter the PIC or average peptide length (FIG. 4B). A forced-flow pepsin microreactor may improve tuning but would likely not generate smaller fragments.

Digestion of Gliadin by Nepenthesin

Figure 5:
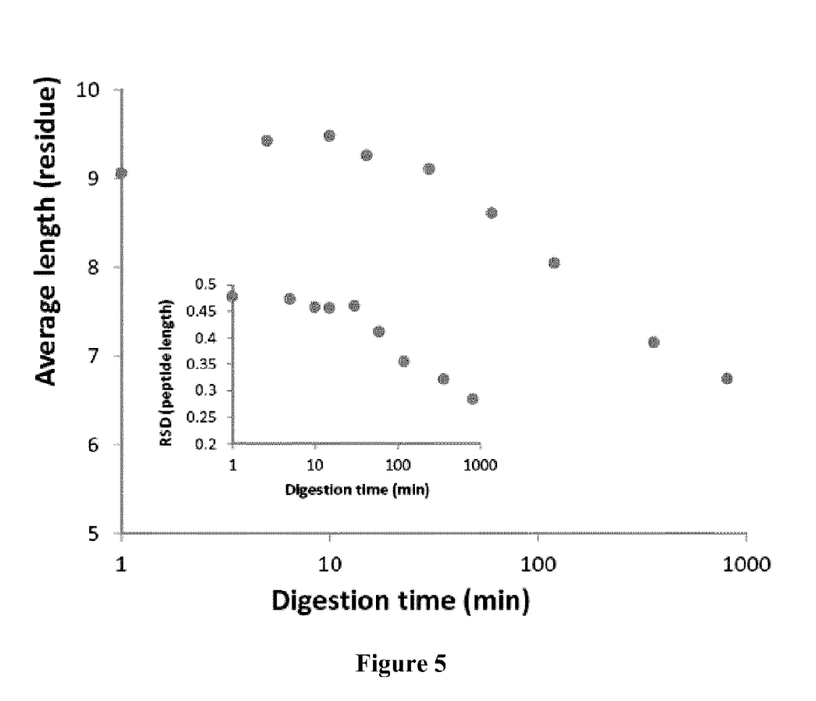
FIG. 5 shows the average length of all peptides identified from a nepenthesin digestion of gliadin from wheat, using LC-MS/MS, after 1, 5, 10, 15, 30, 60, 130, 360 or 810 minutes at 37° C. A 95% confidence cut-off ($p<0.05$) on the scores were used to remove false positive identification. Relative standard deviation of the peptide length is shown in the inset figure.

Digestions gliadin by nepenthesin were performed in solution using a LEAP HTX-PAL autosampler and dispensing system designed for hydrogen/deuterium exchange (HDX) applications. Data were collected using an AB Sciex Triple-TOF 5600 QqTOF mass spectrometer. Peptides were identified using Mascot (v2.3) from MS/MS data. Briefly, 12 pmol of crude gliadin (purchased from Sigma Aldrich) were mixed with 2 μL of 100× concentrated fluid. After digestion the entire volume was injected into a reversed-phase LC system connected to the mass spectrometer. The peptides were trapped on a 7 cm, 150 μm i.d. Magic C18 column and eluted with an acetonitrile gradient from 10% to 40% in 10 or 30 minutes. Peptides detected in these analyses were selected for CID fragmentation in multiple information-dependent acquisitions of MS/MS spectra. Spectra were searched against a miniature database containing the sequences for all identified wheat gliadin (α, β, γ, ω) proteins plus the low and high molecular weight glutenin. FIG. 5 shows the average length of all peptides identified from the nepenthesin digestion of gliadin from wheat, using LC-MS/MS, after 1, 5, 10, 15, 30, 60, 130, 360 or 810 minutes at 37° C. A 95% confidence cut-off (p<0.05) on the scores were used to remove false positive identification. Relative standard deviation of the peptide length is shown in the inset figure.

Figure 6:
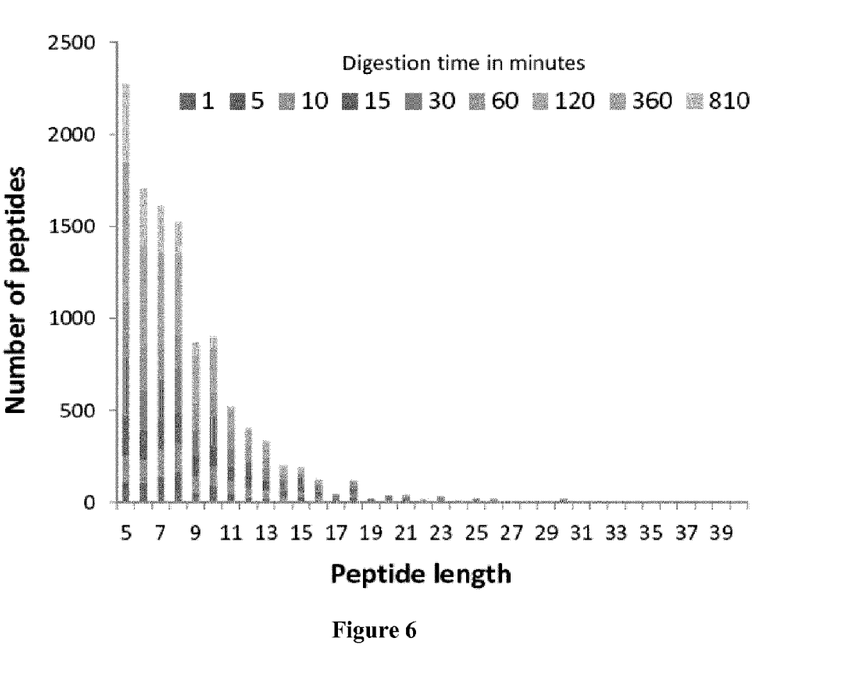
FIG. 6 displays the number of peptides identified by LC-MS/MS after 1, 5, 10, 15, 30, 60, 130, 360 or 810 minutes digestion at 37° C., grouped by length. Data as in FIG. 5.

FIG. 6 displays the number of peptides identified by LC-MS/MS after 1, 5, 10, 15, 30, 60, 130, 360 or 810 minutes digestion at 37° C., grouped by length. Data as in FIG. 5.

Figure 7:
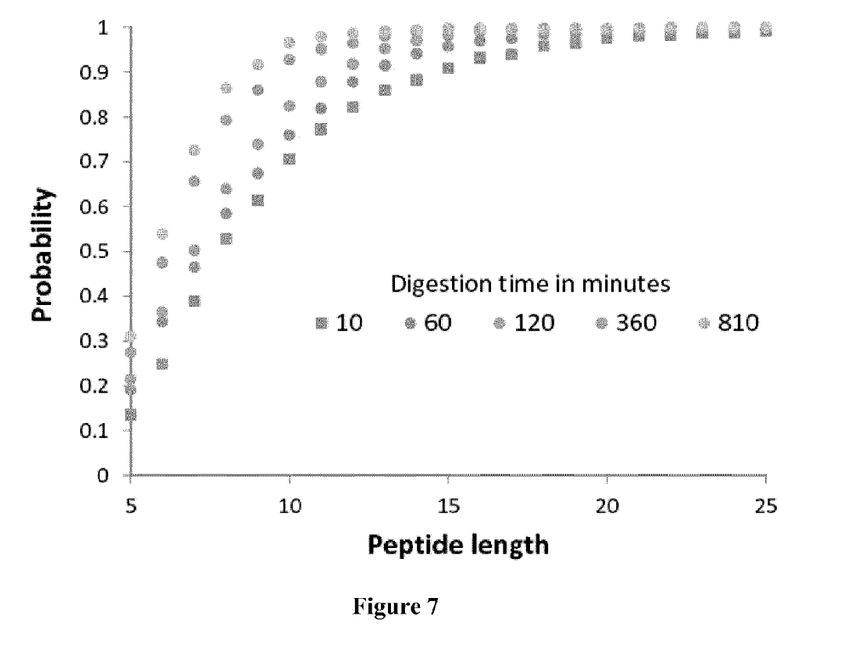
FIG. 7 displays the same data as in FIG. 5, as a probability of obtaining a certain length after 10, 60, 120, 360 or 810 minutes digestion at 37° C.

FIG. 7 displays the same data as in FIG. 5, as a probability of obtaining a certain length after 10, 60, 120, 360 or 810 minutes digestion at 37° C.

Although the foregoing has been described in some detail by way of illustration and example for purposes of clarity of understanding, one of skill in the art will appreciate that certain changes and modifications may be practiced within the scope of the appended claims. In addition, each reference provided herein is incorporated by reference in its entirety to the same extent as if each reference was individually incorporated by reference.

What is claimed is:

1. A solid composition for treating or attenuating gluten intolerance comprising:
   (a) an effective amount of nepenthesin selected from the group consisting of a nepenthesin I salt, a nepenthesin II salt, or a combination thereof, and
   (b) an effective amount of a buffer to maintain the pH of said solid composition at a pH of 5 or above, wherein said nepenthesin is inactive prior to administration; wherein said effective amount of nepenthesin is sufficient to degrade gluten upon oral administration of said solid composition to a patient suffering from gluten intolerance.

2. The solid composition of claim 1, wherein said effective amount of nepenthesin is between about 1 mg and about 1 g, wherein about refers to a variation of up to ±5%.

3. The solid composition of claim 1, further comprising at least one additional agent selected from the group consisting of an inhibitor of a transglutaminase, an anti-inflammatory agent, a COX-2 inhibitor, a p38 MAP kinase inhibitor, a mast cell-stabilizing agent, an anti-ulcer agent, an anti-allergy agent, and an anti-TNF-α agent.

4. The solid composition of claim 1, further comprising at least one additional enzyme selected from the group consisting of a gastric protease, an aspartic protease, and a prolyl endopeptidase.

5. The solid composition of claim 1, wherein said composition is formulated to release said nepenthesin in a patient's stomach.

6. The solid composition of claim 2, wherein said effective amount of said nepenthesin is between about 1 mg and about 500 mg.

7. The solid composition of claim 2, wherein said effective amount of said nepenthesin is between about 1 mg and about 200 mg.

8. The solid composition of claim 1, wherein said gluten intolerance is celiac disease, wheat allergy, gluten sensitivity, or dermatitis herpetiformis.

* * * * *

SEQUENCE LISTING

```
<160> NUMBER OF SEQ ID NOS: 1

<210> SEQ ID NO 1
<211> LENGTH: 341
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 1

Gly Pro Leu Gly Ser Met Glu Arg Lys Ile Ser Arg Ile His Leu Val
1               5                   10                  15

Ser Glu Pro Ser Ile Thr His Phe Leu Gln Val Ser Trp Glu Lys Thr
            20                  25                  30

Leu Glu Ser Gly Phe Val Ile Thr Leu Thr Asp Gly His Ser Ala Trp
        35                  40                  45

Thr Gly Thr Val Ser Glu Ser Glu Ile Ser Gln Glu Ala Asp Asp Met
    50                  55                  60

Ala Met Glu Lys Gly Lys Tyr Val Gly Glu Leu Arg Lys Ala Leu Leu
65                  70                  75                  80
```

```
Ser Gly Ala Gly Pro Ala Asp Val Tyr Thr Phe Asn Phe Ser Lys Glu
            85                  90                  95
Ser Cys Tyr Phe Phe Phe Glu Lys Asn Leu Lys Asp Val Ser Phe Arg
            100                 105                 110
Leu Gly Ser Phe Asn Leu Glu Lys Val Glu Asn Pro Ala Glu Val Ile
            115                 120                 125
Arg Glu Leu Ile Cys Tyr Cys Leu Asp Thr Ile Ala Glu Asn Gln Ala
        130                 135                 140
Lys Asn Glu His Leu Gln Lys Glu Asn Glu Arg Leu Leu Arg Asp Trp
145                 150                 155                 160
Asn Asp Val Gln Gly Arg Phe Glu Lys Cys Val Ser Ala Lys Glu Ala
                165                 170                 175
Leu Glu Thr Asp Leu Tyr Lys Arg Phe Ile Leu Val Leu Asn Glu Lys
            180                 185                 190
Lys Thr Lys Ile Arg Ser Leu His Asn Lys Leu Leu Asn Ala Ala Gln
        195                 200                 205
Glu Arg Glu Lys Asp Ile Lys Gln Glu Gly Glu Thr Ala Ile Cys Ser
    210                 215                 220
Glu Met Thr Ala Asp Arg Asp Pro Val Tyr Asp Glu Ser Thr Asp Glu
225                 230                 235                 240
Glu Ser Glu Asn Gln Thr Asp Leu Ser Gly Leu Ala Ser Ala Ala Val
            245                 250                 255
Ser Lys Asp Asp Ser Ile Ile Ser Ser Leu Asp Val Thr Asp Ile Ala
            260                 265                 270
Pro Ser Arg Lys Arg Arg Gln Arg Met Gln Arg Asn Leu Gly Thr Glu
        275                 280                 285
Pro Lys Met Ala Pro Gln Glu Asn Gln Leu Gln Glu Lys Glu Asn Ser
    290                 295                 300
Arg Pro Asp Ser Ser Leu Pro Glu Thr Ser Lys Lys Glu His Ile Ser
305                 310                 315                 320
Ala Glu Asn Met Ser Leu Glu Thr Leu Arg Asn Ser Ser Pro Glu Asp
            325                 330                 335
Leu Phe Asp Glu Ile
            340
```